United States Patent
Reunamäki et al.

[11] Patent Number: 5,710,182
[45] Date of Patent: Jan. 20, 1998

[54] OPHTHALMIC COMPOSITION

[75] Inventors: Timo Reunamäki; Kari Lehmussaari; Eija Vartiainen; Olli Oksala, all of Tampere; Sakari Alaranta, Kangasala, all of Finland

[73] Assignee: Santen Oy, Tampere, Finland

[21] Appl. No.: 535,037

[22] PCT Filed: Mar. 29, 1995

[86] PCT No.: PCT/FI95/00166

§ 371 Date: Apr. 2, 1996

§ 102(e) Date: Apr. 2, 1996

[87] PCT Pub. No.: WO95/26711

PCT Pub. Date: Oct. 12, 1995

[30] Foreign Application Priority Data

Mar. 31, 1994 [SE] Sweden ................................. 9401108

[51] Int. Cl.$^6$ ................................................. A61K 47/00
[52] U.S. Cl. ........................................ 514/772.3; 514/912
[58] Field of Search ........................... 514/772.3, 912

[56] References Cited

FOREIGN PATENT DOCUMENTS

| | | |
|---|---|---|
| 2839752 | 12/1995 | Germany. |
| WO 9119481 | 12/1991 | WIPO. |
| WO 9300887 | 1/1993 | WIPO. |

OTHER PUBLICATIONS

Florence Thermes et al., "Bioadhesion: The Effect of Polyacrylic Acid on the Ocular Bioavailability of Timolol", 1992, vol. 81, pp. 54–65, International Journal of Pharmaceutica.

*Primary Examiner*—Zohreh Fay

[57] ABSTRACT

The present invention is directed to an ophthalmic composition in the form of a topical aqueous solution consisting essentially of an ophthalmologically active agent, an ion sensitive, hydrophilic polymer in an amount a of 0.004 to 1.5% by weight, at least one salt selected from the group of inorganic salts and buffers in a total amount of from 0.01 to 2.0% by weight, a wetting agent in an amount of 0 to 3.0% by weight, a preservative in an amount of 0 to 0.02% by weight, water, and optionally a pH regulating agent in an amount sufficient to give a pH of 4.0 to 8.0 to the composition, the ratio between salt and polymer components being such that the solution exhibits a viscosity of less than 1000 mPas. The composition contains a sufficient amount of polymer to provide for a controlled absorption of the drug into the eye, its viscosity having been reduced to provide for better handling characteristics.

12 Claims, 1 Drawing Sheet

OPHTHALMIC COMPOSITION

BACKGROUND OF THE INVENTION

The present invention relates to an ophthalmic composition in the form of a topical aqueous solution for human and veterinary use, as well as the use of the solution, especially for the treatment of glaucoma and ocular hypertension.

It is well known to use polymers alone or in combination with other polymers for the preparation of ophthalmic pharmaceuticals and artificial tear compositions. The inclusion of the polymer aims at increasing the viscosity of the composition so as to provide for a longer contact time with the cornea of the eye, and, for example, in connection with ophthalmic drugs, to provide for a sustained release of the drug into the eye.

For example, the U.S. Pat. Nos. 5,075,104 and 5,209,927 relate to an ophthalmic gel composition and an ophthalmic liquid composition, respectively. The first mentioned composition includes 0.25 to 8% by weight of a carboxy vinyl polymer (polymer of carbomer type), the latter 0.05 to 0.25% by weight, resulting in viscosities of the compositions ranging from 15000 to 300000, or 10 to 20000, respectively.

In the publication WO 93/17664 high viscosity, polymer containing ophthalmic compositions are disclosed containing, in combination, carboxy vinyl polymers of the carbomer type, and cellulosic polymers. According to this disclosure lower polymer concentrations can be used while still achieving the desired higher viscosity. A wide range for the concentration of polymers is given, the broadest range indicated being 0.05 to 3% by weight of carbomer, and 0.05 to 5.0% by weight of cellulose polymer. A similar two-polymer system is described in the WO-publication WO 91/19481, the system being such which gels when exposed to the pH and temperature conditions of the eye surface. In the said publication, an inclusion of up to 0.9% of salt is contemplated for the adjustment of the viscosity.

There is also a number of publications relating to pharmaceutically active ophthalmic compositions containing various polymers, i.a. carboxy vinyl polymers, at various concentrations. As tonicity regulating agents, usually non-ionic polyols are suggested so as not to interfere with the gel structure (WO 93/00887, WO 90/13284). In the publication Int. J. Pharm. 81 (1992) 59–65 aqueous compositions containing timolol maleate and 0.6% polyacrylic acid (MW 250,000), as well as the salt of timolol base with 0.6% polyacrylic acid are described, containing mannitol as tonicity regulator. The viscosity measured at low shear rates is indicated as being 45 mPas.

In the DE-patent specification 28 39 752 ophthalmic gel compositions are described containing carboxy vinyl polymers in an amount of 0.05 to 5.0% by weight and exhibiting viscosities of 1000 to 100,000 mPas. According to this disclosure, a small amount of sodium chloride from 0.001 to 0.5% by weight is added in order to prevent the gel from breaking down on the surface of the eye (see column 4, lines 41 ff).

SUMMARY OF THE INVENTION

The present invention is based on the discovery that the beneficial effect of ophthalmic compositions of the above type containing viscosity enhancing agents, is due to the concentration of the polymer present in the composition, rather than on the viscosity thereof. Thus the aim of the invention is to provide an ophthalmic composition with a sufficiently high concentration of polymer to control the formation of the polymer film on the cornea of the eye, but which composition is still fluid enough for ocular topical application. A further object of the invention is to provide an easy-to-use eye drop formulation with improved patient compliance.

According to the invention it has now been shown that by raising the concentration of the polymer over a value where the composition normally is a gel rather than a liquid and by simultaneously lowering the viscosity thereof, it is possible to obtain a desired beneficial effect of the active agent in the eye, while simultaneously reducing any discomfort in the patient's eye, as compared to the administration of a composition in gel form. The unbroken and even polymer film still being formed on the eye facilitates the binding and retaining of water on the surface of the eye, and thus provides for an additional wetting effect while providing for a better contact and thus a controlled absorption of active agent into the eye.

The present invention thus provides an ophthalmological composition in a liquid, easy-to-use form which contains a sufficient amount of polymer to provide for both an increased and prolonged absorption of active agent into the eye. The invention thus makes it possible to treat e.g. glaucoma and ocular hypertension using a once-a-day-only or less frequent regimen for administering the ophthalmological active agent, and to lower the dosage clearly below the dosages presently in use.

According to the invention we have shown that it is the amount of polymer in the composition, rather than the viscosity of the composition as such, which are important from the point of view of obtaining good absorption of drug into the eye. This is especially evident from the tests described below. In the FIG. 2 it is shown, for example, that by using the same amount of polymer, in compositions that have different viscosities, the compositions provide for substantially the same absorption. According to the state of the art one would, however, had expected the composition with the higher viscosity to provide for the higher absorption.

More specifically, the object of the invention is an ophthalmic composition in the form of a topical aqueous solution consisting essentially of an ophthalmologically active agent, an ion sensitive, hydrophilic polymer in an amount of 0.004 to 1.5% by weight, at least one salt selected from the group of inorganic salts and buffers in a total amount of from 0.01 to 2.0% by weight, a wetting agent in an amount of 0 to 3.0% by weight, a preservative in an amount of 0 to 0.02% by weight, water, and optionally a pH regulating agent in an amount sufficient to give a pH of 4.0 to 8.0 to the composition, the ratio between salt and polymer components being such that the solution exhibits a viscosity of less than 1000 centipoise.

DETAILED DESCRIPTION OF THE INVENTION

Figure 1:
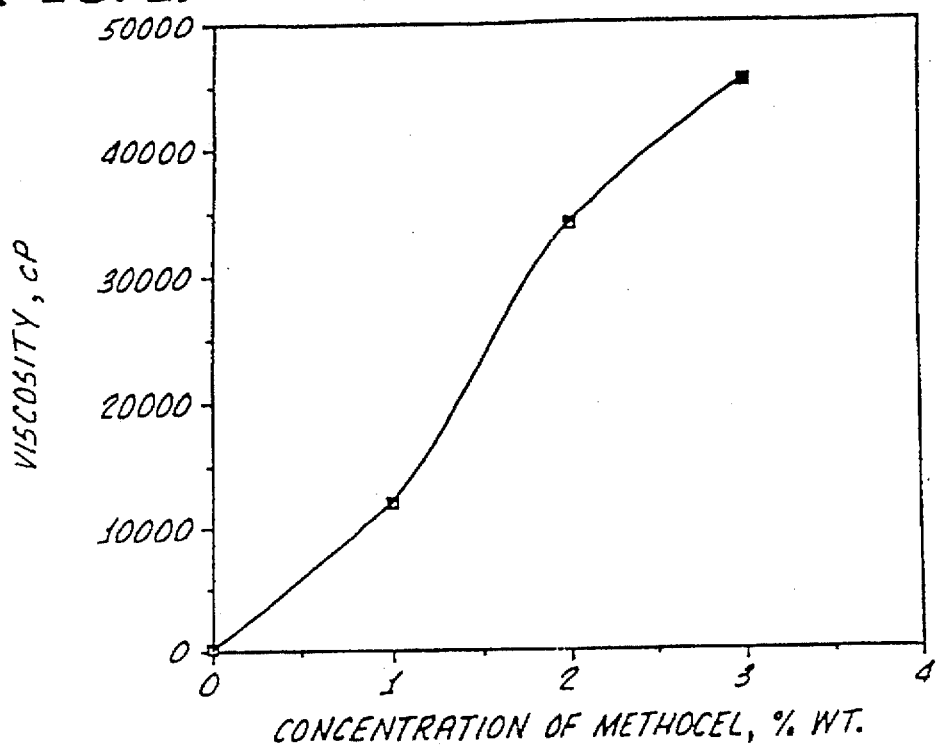
FIG. 1 shows viscosity versus shear rate curves.

The ion-sensitive hydrophilic polymer to be used according to the invention contains acid groups, and is typically a carboxy vinyl polymer, or hyaluronic acid. Typical representatives of carboxy vinyl polymers are the polyacrylic acid polymers, known as carbomers. Carbomers are available at different molecular weights, typically ranging from e.g. 450.000 to 4.000.000, and sold under the trade name Carbopol, e.g. Carbopol 907, 910, 934, 934P, 940, 941, 971, 971P, 974, 974P, 980, and 981, preferably Carbopol 941 and 981.

The polymer is preferably used in an amount of 0.01 to 0.8, more preferably 0.01 to 0.4, and advantageously 0.04 to 0.4% by weight.

According to the invention it has been established that it is favourable both from the view point of efficacy of the product in the target site, and of ease of application, to reduce the viscosity of the composition to a level of less than 1000 centipoise, suitably less than 500 centipoise, when measured at 25° C. with a Brookfield LVDV-III type viscometer at a shear rate D of $1.1\ s^{-1}$. This object is achieved by adding to the composition a salt and/or a buffer in the specified amount, preferably in an amount of 0.01 to 1.5% by weight. As viscosity decreasing salts and buffers, i.a. the following may be mentioned: sodium chloride, potassium chloride, sodium phosphates (monobasic and dibasic), sodium borate, sodium acetate, and sodium citrate, as well as their equivalents and mixtures thereof. In case no salts are added, a formulation with an unacceptably high viscosity is obtained.—It is to be noted that the composition according to the invention still exhibits favourable non-newtonian properties when applied to the eye surface, despite the addition of salts.

For some purposes, for example for appearance and storage purposes, the use of a buffering salt is preferred to the use of e.g. sodium or potassium chloride as the viscosity reducing agent.

In case the active agent contains basic groups, such as amine groups, an additional beneficial effect is achieved when using polymers containing acid groups, such as carboxy groups, due to the ion exchange reaction or salt formation between the acidic polymer and the basic active agent. The increased retaining ionic forces between the polymer and active agent thus provides for improved delivery of the active agent. Due to the fact that the basic drug is well retained by the polymer, the dosage can be lowered and/or the daily number of administration of the drug can be reduced, if desired, without the loss of activity, and consequently the side effects can be reduced as well.

The pH of the composition is suitably from 5.0 to 8, preferably from 6.5 to 8.0. When using a base as the active agent, the pH of the composition can be regulated by the amounts used of acidic polymer and basic active agent respectively. However, if necessary, the pH of the composition may be adjusted also by adding an additional base or an acid, as the case may be, such as an alkali metal hydroxide, especially sodium hydroxide, or ammonium hydroxide, or e.g. hydrochloric acid.

The ophthalmologically active agent is advantageously an antiglaucoma agent, a sympathomimetic agent, a sympatholytic agent, such as a β-blocker, a carbonic anhydrase inhibitor, or an antibiotic, antiinflammatoric, antiallergic agent, etc., or a combination thereof. Preferably an agent active against glaucoma or effective in the treatment of increased intraocular pressure is used.

As stated above, especially contemplated within the scope of the invention is the use of an amine group containing pharmaceutically active agent. Thus according to the invention, the eye drugs contemplated may contain a primary, secondary or tertiary amino group or organoammonium or amidine attached to a chain or a ring, or a nitrogen atom(s) can be a part in various basic heterocycles, such as imidazole, imidazoline, pyridine, piperidine or piperazine. Preferably an agent active against glaucoma or effective in the treatment of increased intraocular pressure is used. A particularly preferred group of compounds is comprised of β-blocking agents having a secondary amine function such as betaxolol, carteolol, levobunolol, metipranolol, pindolol, propranolol and timolol, as such or in the form of their acid addition salts. An especially advantageous mode of the invention is such where timolol is used as its easily crystallizable S-timolol maleate or hemihydrate.

Other typical examples of basic drug molecules useful in eye therapy in the advantageous mode of the invention include tobramycin and norfloxacin (antimicrobial, antibacterial), cyclopentolate, tropicamide, atropine, phenylephrine, metaoxedrine (anticholinergic, mydriatic), pilocarpine, carbacol, ecothiopate (cholinergic), adrenaline, dipivefrin, dopamine (adrenergic), naphazoline, tetryzoline (vasoconstrictor), verapamil, nifedipine (vasodilator), apraclonidine, clonidine, medetomidine ($\alpha_2$-agonist), sezolamide (carbonic anhydrase inhibitor), cetirizine (antihistamine), as such or in their acid addition, ester and prodrug forms.

Especially contemplated in the invention is the use of a β-blocking agent, such as S-timolol, as the only drug, or as combined with e.g. the base form of pilocarpine.

The amount of active agent in the final composition may vary, such as between 0.001 to 5% by weight, usually however between 0.01 to 0.5% by weight, and typically between 0.1 and 0.5% by weight, especially in the case of S-timolol.

According to an advantageous embodiment of the invention, the composition contains in addition, in order to enhance the wetting effect thereof, a wetting agent, preferably a polyhydric alcohol, such as glycerol. The amount of wetting agent is generally at the most 3.0%, such as of the order of 0.5 to 3.0% by weight.

As preservatives, e.g. benzalkonium chloride, benzyl alcohol, mercury salts, thiomersal, chlorhexidine or the like, as such or in combination. The amount of preservative usually lies in the range of 0 to 0.02% by weight.

A preferred composition according to the invention in the form of an aqueous solution consists essentially of the following components (% being% by weight of the total composition):

timolol in the form of its maleate salt or hemihydrate in an amount of 0.1 to 0.5% by weight, calculated as the free base,
polyacrylic acid in an amount of 0.04 to 0.4% by weight
glycerol in an amount of 0.5 to 2.5% by weight
sodium phosphates in an amount of 0.01 to 1.5% by weight,
a preservative in an amount of 0 to 0.02%,
water, and optionally
a pH-regulating agent to give the composition a pH of 6.5 to 8.0, and wherein the viscosity of the solution is less than 800 centipoise.

According to the invention, the term "consisting essentially of" is intended to mean that the composition contains only or essentially only the components listed in connection therewith. The compositions may, however, in addition, contain ophthalmologically acceptable additives and adjuvants of such type and amounts as to have no essential influence on the characteristics of the composition.

The composition according to the invention is typically prepared in three stages. In the first step the polymer is dispersed in sterile water and sterilized by autoclaving. In the second step, the other ingredients, namely the active ingredient(s), inorganic salt(s), tonicity regulating agent(s), preservative(s) and any other additives, are dissolved in sterile water and sterilized by filtration on a filter (pore size e.g. 0.2 μm). In the third and last step the solution prepared in the two steps are combined aseptically and mixed until they form a homogenous solution with a low viscosity. The pH of the solution may be adjusted, if necessary, by adding a base or an acid. Thereafter the composition is packaged in multi- or unit dose form.

The following examples illustrate the invention in more detail, without limiting the same.

EXAMPLE 1

The following composition was made:

| Composition | (g) |
| --- | --- |
| S-Timolol hemihydrate | 2.56 |
| Carbopol 941 | 0.95 |
| Sodium phosphate monobasic | 0.08 |
| Sodium phosphate dibasic | 1.80 |
| Glycerol | 23.0 |
| Benzalkonium chloride | 0.06 |
| Water for injection | to 1000 mL |

Carbopol 941 was dispersed in 300 mL sterile water at room temperature. The solution was sterilized in an autoclave. The autoclaved solution was cooled to room temperature (solution 1). Benzalkonium chloride, glycerol, sodium phosphate monobasic and dibasic and timolol hemihydrate were dissolved in 700 mL sterile water at room temperature and sterilized by filtration on a filter with a pore size of 0.2 μm (solution 2). In the final step the solutions prepared in the two previous steps (solution 1 and 2) were combined aseptically and mixed until they formed a homogenous low viscous solution. The pH of the solution obtained was 7.4 and its viscosity was 440 centipoise (D=1.1 s$^{-1}$). Thereafter the solution was packed in traditional eye drop bottles.

The viscosity vs. shear rate curve for the composition is shown in FIG. 1. It is to be noted that the shape of the curve shows still non-newtonian rheology despite the addition of salts.

EXAMPLE 2

The following composition was made:

| Composition | (g) |
| --- | --- |
| S-Timolol maleate | 3.42 |
| Carbopol 941 | 2.00 |
| Sodium chloride | 3.5 |
| Glycerol | 15.0 |
| Benzalkonium chloride | 0.06 |
| Sodium hydroxide | q.s. ad pH 7.5 |
| Water for injection | to 1000 mL |

The solution was prepared according to the Example 1 except that the pH of the solution was adjusted to pH 7.5 by adding the sterile filtered sodium hydroxide solution. The viscosity of the solution was 430 centipoise (D=1.1 s$^{-1}$). Viscosity vs. shear rate curve is shown in FIG. 1.

EXAMPLE 3

The following composition was made:

| Composition | (g) |
| --- | --- |
| S-Timolol hemihydrate | 2.56 |
| Carbopol 981 | 1.4 |
| Sodium phosphate monobasic | 0.62 |
| Sodium phosphate dibasic | 2.85 |
| Glycerol | 23.0 |
| Benzalkonium chloride | 0.06 |
| Water for injection | to 1000 mL |

The solution was prepared according to the Example 1. The pH of the solution obtained was 6.9 and the viscosity of the solution was 70 centipoise (D=1.1 s$^{-1}$). Viscosity vs. shear rate curve is shown in FIG. 1.

EXAMPLE 4

The following composition was made:

| Composition | (g) |
| --- | --- |
| S-Timolol hemihydrate | 1.02 |
| Carbopol 941 | 2.28 |
| Sodium phosphate monobasic | 1.55 |
| Sodium phosphate dibasic | 7.10 |
| Glycerol | 20.0 |
| Sodium hydroxide | q.s. ad pH 6.8 |
| Water for injection | to 1000 mL |

The solution was prepared according to the Example 1. The pH of the solution was adjusted to pH 6.8 with a sodium hydroxide solution. The viscosity of the solution was 590 centipoise (D=1.1 s$^{-1}$).

EXAMPLE 5

The following composition was made:

| Composition | (g) |
| --- | --- |
| S-Timolol maleate | 6.84 |
| Carbopol 941 | 3.0 |
| Sodium phosphate monobasic | 0.59 |
| Sodium phosphate dibasic | 8.24 |
| Benzalkonium chloride | 0.1 |
| Sodium hydroxide | q.s. ad pH 7.2 |
| Water for injection | to 1000 mL |

The solution was prepared according to the Example 1. The pH of the solution was adjusted to pH 7.2 with sodium hydroxide and the viscosity of the solution was 270 centipoise (D=1.1 s$^{-1}$).

EXAMPLE 6

The following composition was made:

| Composition | (g) |
| --- | --- |
| Clonidine (base) | 1.25 |
| Carbopol 981 | 0.70 |
| Sodium phosphate monobasic | 0.04 |
| Sodium phosphate dibasic | 0.6 |
| Glycerol | 23.0 |

-continued

| Composition | (g) |
|---|---|
| Benzalkonium chloride | 0.06 |
| Water for injection | to 1000 mL |

The solution was prepared according to the Example 1. The pH of the solution obtained was 7.0 and the viscosity was 540 centipoise (D=1.1 s$^{-1}$).

EXAMPLE 7

The following composition was made:

| Composition | (g) |
|---|---|
| Pilocarpine (base) | 20.0 |
| Carbopol 981 | 3.0 |
| Sodium phosphate monobasic | 10.6 |
| Sodium phosphate dibasic | 0.53 |
| Glycerol | 5.0 |
| Benzalkonium chloride | 0.10 |
| Water for injection | to 1000 mL |

The solution was prepared according to the Example 1. The pH of the solution obtained was 6.8 and the viscosity was 900 centipoise (D=1.1 s$^{-1}$).

By leaving out from the formulations (Examples 1–3, 5–7) the benzalkonium chloride, corresponding unit-dose formulations were obtained.

By adding to the formulations (Example 4) benzalkonium chloride 0.06 mg/ml, a corresponding multidose-formulation was obtained.

Absorption of timolol into the rabbit eye (Study 1)

An ophthalmic formulation (Example 1), which is a typical example of this invention, was instilled into a rabbit eye (n=6). The concentration of timolol in the aqueous humor was measured after ½ and 1 hours using HPLC. The reference product contained the same amount of Carbopol, timolol and preservative, benzalkonium chloride, but did not contain any inorganic salt(s). The viscosity of the reference product was much higher (7300 centipoise, D=1.1 s$^{-1}$).

Figure 2:
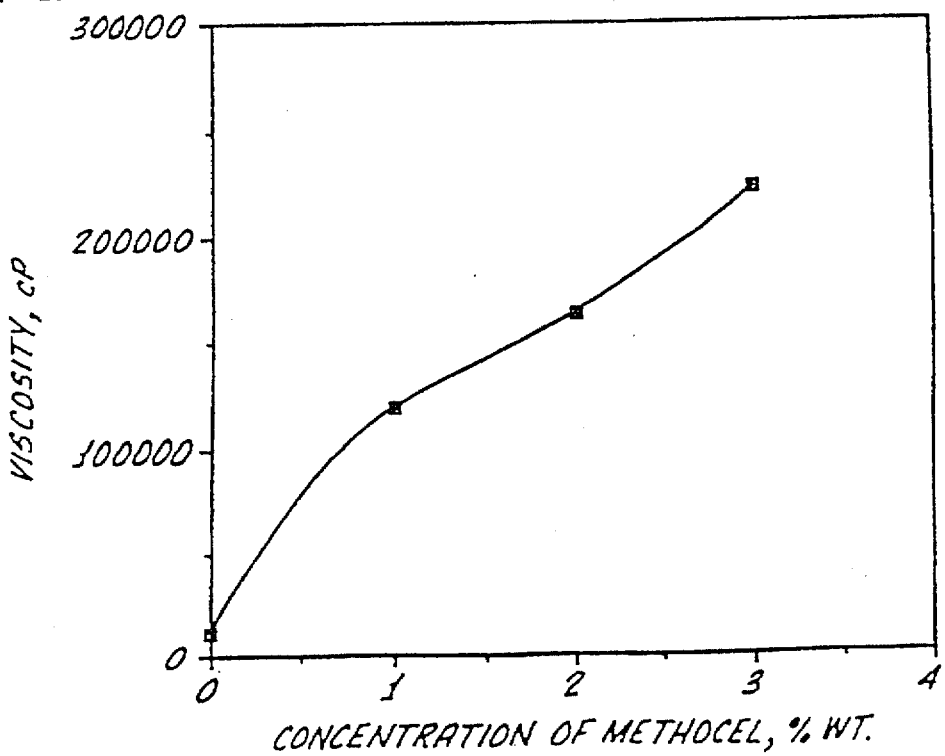
FIG. 2 shows timolol concentration in the aqueous humor in rabbits.

The timolol concentrations in the aqueous humor in rabbits are shown in FIG. 2. According to FIG. 2, the absorption of timolol in rabbits eye was equal despite the different viscosities.

We claim:

1. Ophthalmic composition in the form of a topical aqueous solution consisting essentially of an opthalmologically active agent, an ion sensitive, hydrophilic polymer in an amount of 0.004 to 1.5% by weight, at least one salt selected from the group of inorganic salts and buffers in a total amount of from 0.01 to 2.0% by weight, a wetting agent in an amount of 0 to 3.0% by weight, a preservative in an mount of 0 to 0.02% by weight, water, and where the composition has a pH outside the range of 4.0 to 8.0, a pH regulating agent in an amount sufficient to give a pH of about 4.0 to about 8.0 to the composition, the ratio between salt and polymer being such that the solution exhibits a viscosity of less than 1000 centipoise.

2. The composition of claim 1, wherein the polymer is present in an amount of from 0.01 to 0.8% by weight and is selected from the group consisting of carbopol 907, 910, 934, 934P, 940, 941, 971, 971P, 974, 074P, 980 and 981.

3. The composition of claim 1 wherein the wetting agent is glycerol.

4. The composition of claim 3, wherein the amount of glycerol is 0.5 to 2.5% by weight.

5. The composition of claim 1 or 2, wherein the salt is selected from the group consisting of sodium chloride, potassium chloride, sodium phosphates, sodium borate, sodium acetate, sodium citrate, equivalents and mixtures thereof.

6. The composition of claim 1 or 2, wherein the viscosity is less than about 800 centipoise.

7. The composition of claim 1 or 2, having a pH of 5.0 to 8.0.

8. The composition of claim 1 or 2, wherein the ophthalmologically active agent is selected from the group consisting of antiglaucoma agents, sympathomimetic agents, sympatholytic agents, β-blockers, carbonic anhydrase inhibitors, antibiotics, antiinflammatoric agents, antiallergic agents and mixtures thereof.

9. The composition of claim 8, wherein the pharmaceutically active agent is selected from the group consisting of betaxolol, carteolol, levobunolol, metipranolol, pindolol, propranolol and timolol, pilocarpine and mixtures thereof.

10. The composition of claim 1, consisting essentially of timolol in the form it its maleate salt or its hemihydrate in an amount of 0.1 to 0.5% by weight, calculated as the free base, polyacrylic acid in an amount of 0.04 to 0.4% by weight glycerol in an amount of 0.5 to 2.5% by weight sodium phosphates in an amount of 0.01 to 1.5% by weight, a preservative in an amount of 0 to 0.02% water, and, where the composition has a pH outside the range of 6.5 to 8, a pH-regulating agent in an amount sufficient to provide a pH of 6.5 to 8 of the composition wherein the viscosity of the solution is less than about 800 centipoise.

11. The composition of claim 10, the pH-regulating agent being selected from the group consisting of organic and inorganic bases and acids.

12. The composition of claim 11, wherein the pH-regulating agent is sodium hydroxide.

* * * * *

UNITED STATES PATENT AND TRADEMARK OFFICE
CERTIFICATE OF CORRECTION

Page 1 of 3

PATENT NO. : 5,710,182
DATED : January 20, 1998
INVENTOR(S): REUNAMAKI, Timo; LEHMUSSAARI, Kari; VARTIAINEN, Eija; OKSALA, Olli; ALARANTA, Sakari; POHJALA, Esko It is certified that error appears in the above-identified patent and that said Letters Patent is hereby corrected as shown below:

In the Figures, replace "Fig. 1" with the following:

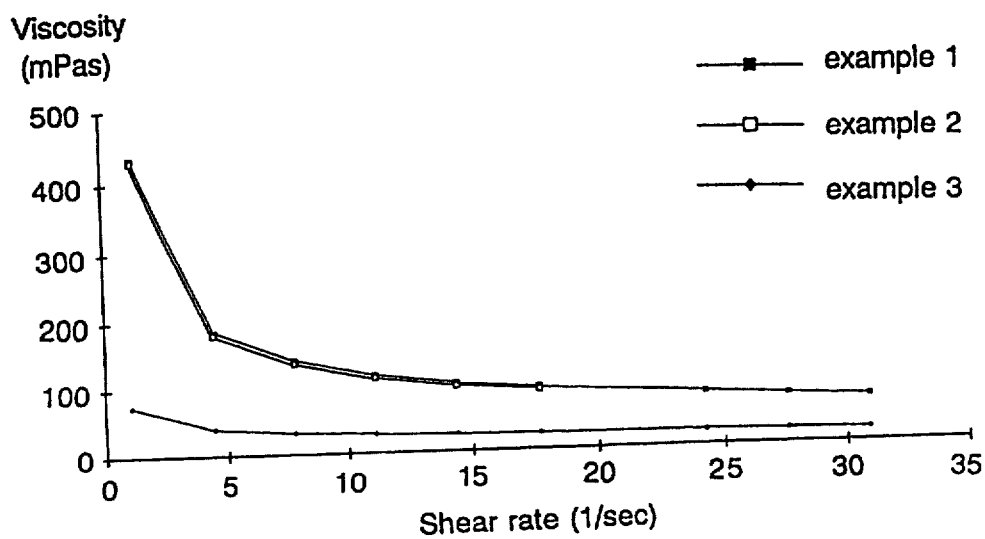

FIG. 1

UNITED STATES PATENT AND TRADEMARK OFFICE

CERTIFICATE OF CORRECTION

PATENT NO. : 5,710,182
DATED : January 20, 1998
INVENTOR(S): REUNAMAKI, Timo; LEHMUSSAARI, Kari; VARTIAINEN, Eija; OKSALA, Olli; ALARANTA, Sakari; POHJALA, Esko It is certified that error appears in the above-identified patent and that said Letters Patent is hereby corrected as shown below:

In the Figures, replace "Fig. 2" with the following:

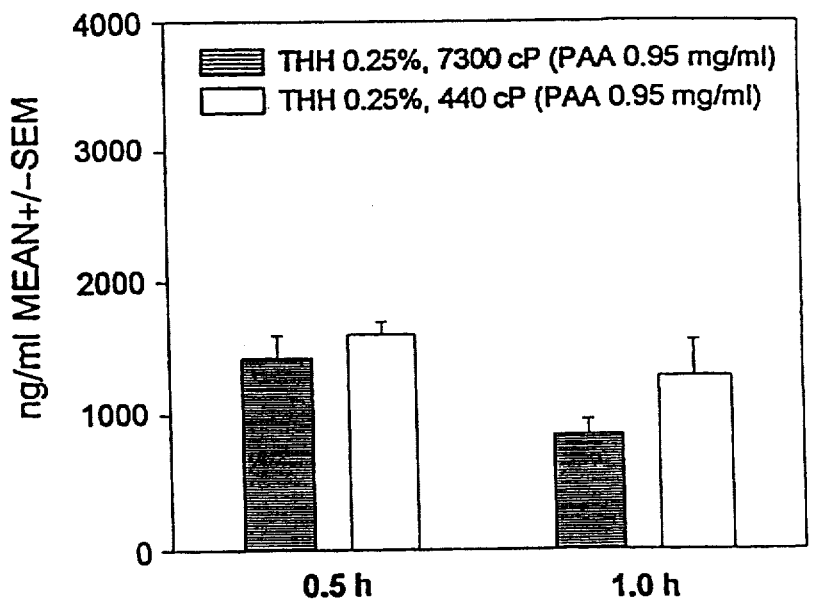

UNITED STATES PATENT AND TRADEMARK OFFICE

CERTIFICATE OF CORRECTION

PATENT NO. : 5,710,182

DATED : January 20, 1998

INVENTOR(S): REUNAMAKI, Timo; LEHMUSSAARI, Kari; VARTIAINEN, Eija; OKSALA, Olli; ALARANTA, Sakari; POHJALA, Esko It is certified that error appears in the above-identified patent and that said Letters Patent is hereby corrected as shown below:

Title page, item [57],
In the Abstract, line 7, replace "inor ganic" with --inorganic--. Column 4, line 48, replace "being%" with --being %--.

In the cover, in [75] include --POHJALA, Esko--.

Signed and Sealed this

Twenty-eighth Day of July, 1998

Attest:

BRUCE LEHMAN

*Attesting Officer*   *Commissioner of Patents and Trademarks*